United States Patent [19]

VandenBerg

[11] Patent Number: Plant 6,883

[45] Date of Patent: Jun. 27, 1989

[54] CHRYSANTHEMUM PLANT NAMED FASTO

[75] Inventor: Cornelis P. VandenBerg, Salinas, Calif.

[73] Assignee: Yoder Brothers, Inc., Barberton, Ohio

[21] Appl. No.: 173,085

[22] Filed: Mar. 25, 1988

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Fasto particularly characterized by its flat capitulum form; daisy capitulum type; greyed-orange ray floret color; diameter across face of capitulum of up to 6 cm at maturity; uniform eight week photoperiodic flowering response to short days; peduncle length ranging from 6 to 15 cm on open, terminal sprays; tall plant height when grown as a single stem spray cut mum; and excellent tolerance to low temperatures for bud initiation and flower development.

3 Drawing Sheets

The present invention comprises a new and distinct cultivar of Chrysanthemum, botanically known as *Dendranthema grandiflora,* and referred to by the cultivar name Fasto.

Fasto, identified as 84105005, was originated from a cross made by Cornelis P. VandenBerg in a controlled breeding program in Salinas, Calif. in 1983.

The female parent and the male parent of Fasto were both unnamed seedlings, identified respectively as 79T34012 and 77358001.

Fasto was discovered and selected as one flowering plant within the progeny of the stated cross by Cornelis P. VandenBerg in August 1984 in a controlled environment in Salinas, Calif.

The first act of asexual reproduction of Fasto was accomplished when vegetative cuttings were taken from the initial selection in October 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Fasto are firmly fixed and are retained through successive generations of asexual reproduction.

Fasto has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Fasto, which, in combination, distinguish this Chrysanthemum as a new and distinct cultivar:

1. Flat capitulum form.
2. Daisy capitulum type.
3. Greyed-orange ray floret color.
4. Diameter across face of capitulum up to 6 cm at maturity.

5. Uniform eight week photoperiodic flowering reponse to short days.
6. Peduncle length ranging from 6 to 15 cm on open terminal sprays.
7. Tall plant height, requiring seven long days prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Fasto, with the colors being as nearly true as possible with illustrations of this type.

Sheet 1 is a color photograph of Fasto grown as a single stem cut spray mum.

Sheet 2 is a black and white photograph of three views of the inflorescence of Fasto.

Sheet 3 is a black and white photograph showing the upper and under sides of the leaves of Fasto at three stages of development (mature, intermediate and immature).

Of the commercial cultivars known to the inventor, the most similar in comparison to Fasto is Amber, disclosed in U.S. Plant Pat. No. 3,969. Reference is made to Chart A, which compares certain characteristics of Fasto to the same characteristics of Amber.

Similar traits are capitulum form and type, and flowering response. The peduncle length of Fasto is slightly shorter, the diameter of capitulum is smaller, and low temperature tolerance is better than Amber. Fasto requires fewer long days than Amber to attain a plant height of 90 to 100 cm.

In the following description, color references are made to the Royal Horticultural Society Colour Chart. The color values were determined on plant material grown in Salinas, Calif. on Oct. 8, 1987.

Classification:

*Botanical.*—*Dendranthema grandiflora,* cv Fasto.

*Commercial.*—Daisy cut spray mum.

INFLORESCENCE

A. Capitulum:

*Form.*—Flat.

*Type.*—Daisy.

*Diameter across face.*—Up to 6 cm at maturity.

B. Corolla of ray florets:

*Color (general tonality from a distance of three meters).*—Greyed-orange.

*Color (upper surface).*—169B fading to 169C.

*Color (under surface).*—12A overlaid with 169D.

*Shape.*—Flat; oblong.

C. Corolla of disc florets:

*Color (mature).*—Closest to 13B.

*Color (immature).*—Closest to 144A.

D. Reproductive organs:

*Androecium.*—Present on disc florets only; abundant pollen.

*Gynoecium.*—Present on both ray and disc florets.

PLANT

A. General appearance:

*Height.*—Tall; 90 to 100 cm as a single stem cut mum with 7 long days prior to short days.

B. Foliage:

*Color (upper surface).*—137A.

*Color (under surface).*—137C.

*Shape.*—Deeply lobed and serrated.

CHART A

COMPARISON OF FASTO AND AMBER

| | Fasto | Amber |
|---|---|---|
| Ray floret color | Greyed-orange | Bronze |
| Capitulum form and type | Flat Daisy | Flat Daisy |
| Spray formation | Terminal 6 to 15 cm peduncles | Terminal 8 to 15 cm peduncles |
| Diameter across face of capitulum | Up to 6 cm | 70 to 82 mm |
| Plant height | 90–100 cm with 7 long days | 90–100 cm with 14 long days |
| Flowering response period | 8 weeks | 8 weeks |
| Low temperature tolerance | Excellent | Poor |

COMPARISONS MADE OF PLANTS GROWN AS SINGLE STEM SPRAY CUT MUMS IN SALINAS, CALIFORNIA

I claim:

1. A new and distinct Chrysanthemum plant named Fasto, as described and illustrated, and parts thereof.

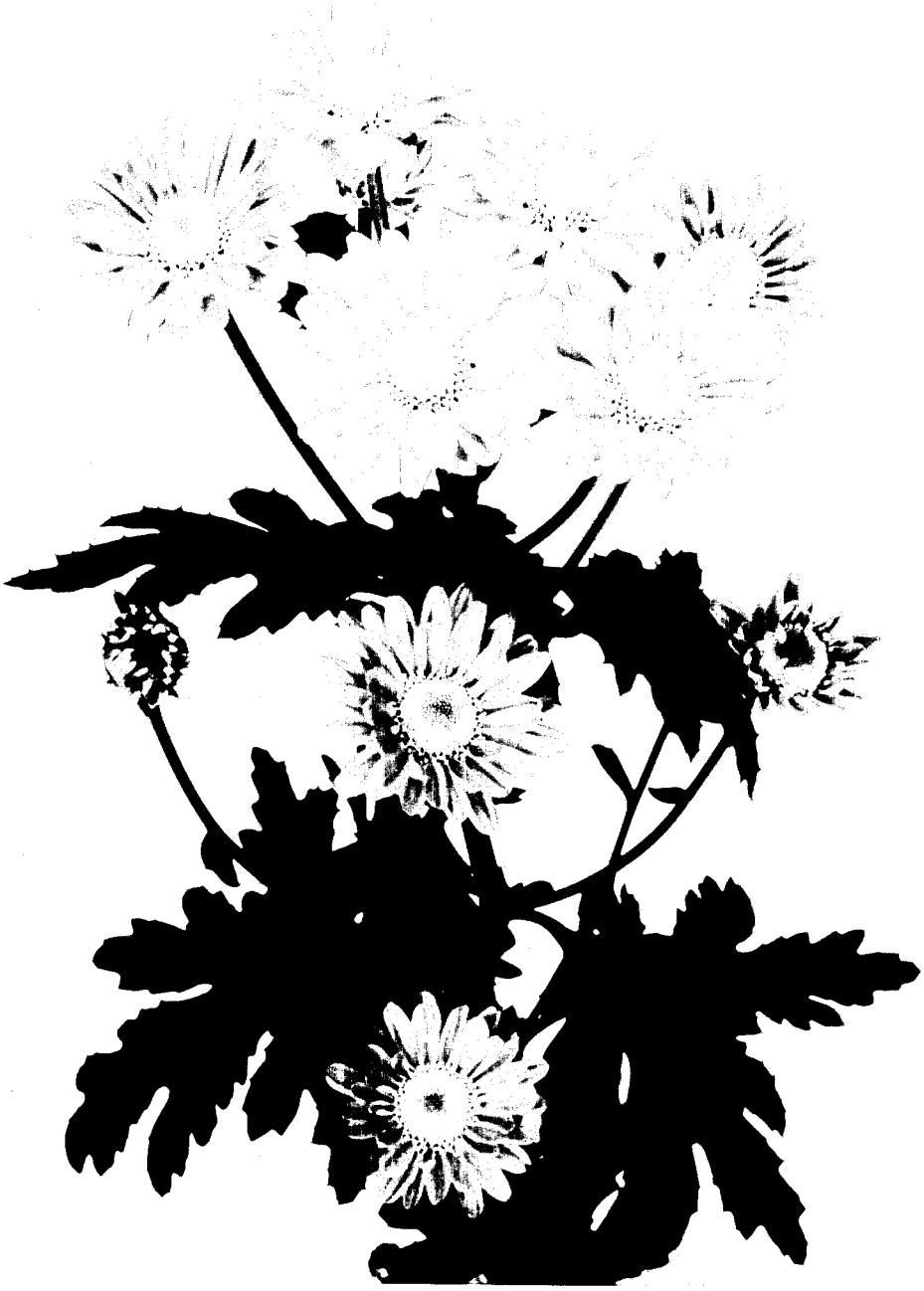

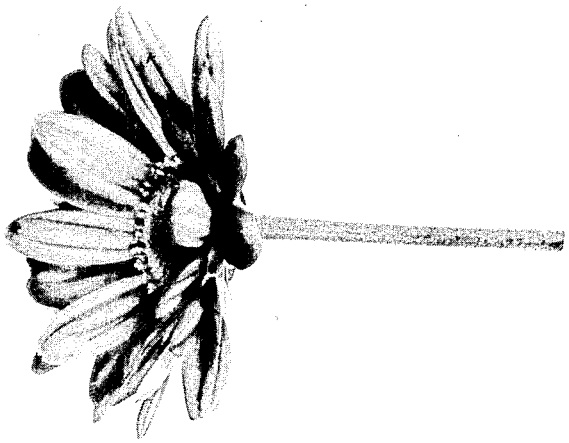
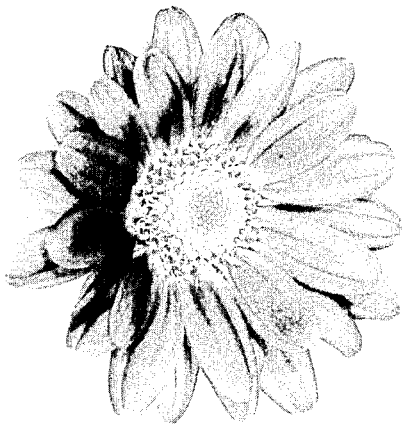
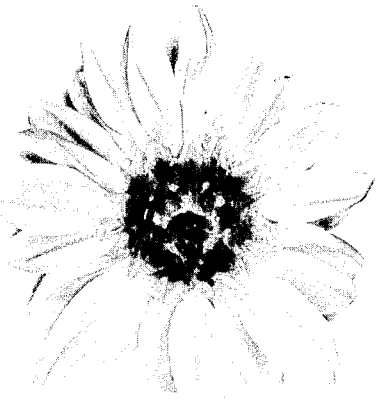

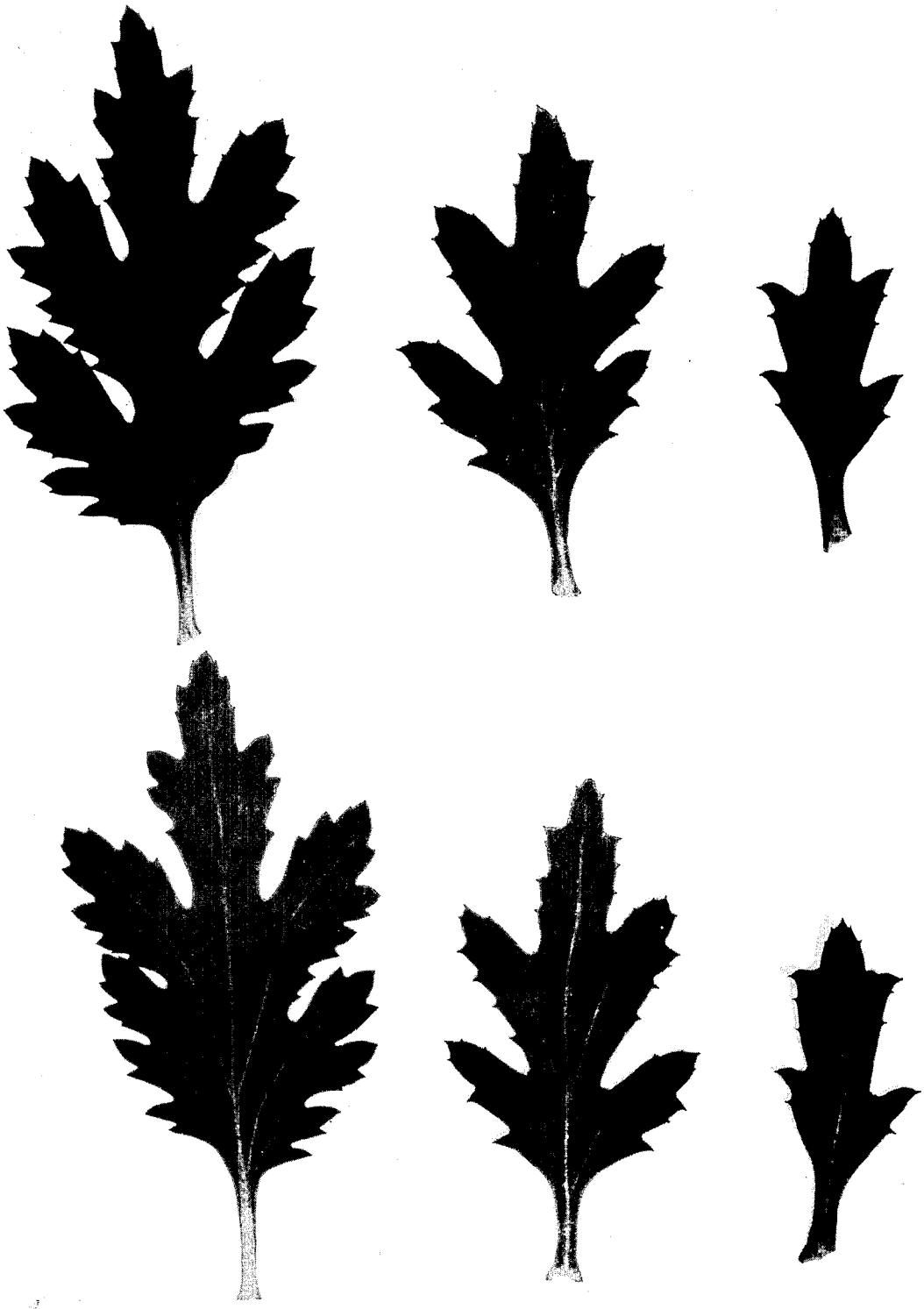

* * * * *